(12) United States Patent
Thompson et al.

(10) Patent No.: US 10,466,144 B2
(45) Date of Patent: Nov. 5, 2019

(54) MULTI-SOURCE, FLOW-WEIGHTED COMPOSITE SAMPLE SYSTEM

(71) Applicant: Mustang Sampling, LLC, Ravenswood, WV (US)

(72) Inventors: Kenneth O. Thompson, Ravenswood, WV (US); Kevin Warner, The Woodlands, TX (US); Timothy L. Querrey, Ravenswood, WV (US)

(73) Assignee: Mustang Sampling, LLC, Ravenswood, WV (US)

( * ) Notice: Subject to any disclaimer, the term of this patent is extended or adjusted under 35 U.S.C. 154(b) by 0 days.

(21) Appl. No.: 16/137,135

(22) Filed: Sep. 20, 2018

(65) Prior Publication Data

US 2019/0101475 A1 Apr. 4, 2019

Related U.S. Application Data

(60) Provisional application No. 62/565,865, filed on Sep. 29, 2017.

(51) Int. Cl.

| | |
|---|---|
| *G01N 1/10* | (2006.01) |
| *G01N 30/12* | (2006.01) |
| *G01N 1/22* | (2006.01) |
| G01N 1/26 | (2006.01) |
| G01N 30/02 | (2006.01) |
| G01N 1/00 | (2006.01) |

(52) U.S. Cl.
CPC ............. *G01N 1/10* (2013.01); *G01N 1/2247* (2013.01); *G01N 30/12* (2013.01); *G01N 1/26* (2013.01); *G01N 2001/002* (2013.01); *G01N 2001/1093* (2013.01); *G01N 2030/025* (2013.01)

(58) Field of Classification Search
CPC ...... G01N 1/10; G01N 1/26; G01N 2001/002; G01N 2001/1093
See application file for complete search history.

(56) References Cited

U.S. PATENT DOCUMENTS

| | | |
|---|---|---|
| 4,396,299 A | 8/1983 | Clingman, Jr. et al. |
| 4,911,006 A | 3/1990 | Hargarten et al. |
| RE35,874 E | 8/1998 | Neeser et al. |

(Continued)

OTHER PUBLICATIONS

International Search Report & Written Opinion of the International Searching Authority, dated Mar. 7, 2019.

*Primary Examiner* — Nathaniel J Kolb
(74) *Attorney, Agent, or Firm* — Cahn & Samuels, LLP

(57) ABSTRACT

A sampling device having at least two inputs each configured to receive samples from a corresponding feedstock input line and a sample accumulator. The device also includes a mass flow controller associated with each feedstock input line, each mass flow controller having a sample output and being configured to receive a signal representative of the flow rate at each input, where each mass flow controller adjusts the flow rate of its respective sample from its respective sample output in response to receiving representative signals. Further the device includes at least a first and second sample output line respectively connected with a sample output of each mass flow controller, each sample output line being connected to an input of the sample accumulator for introduction to the sample accumulator of samples from the output of the mass flow controllers.

18 Claims, 3 Drawing Sheets

(56) References Cited

U.S. PATENT DOCUMENTS

| | | | |
|---|---|---|---|
| 6,505,524 B1 * | 1/2003 | Silvis | G01N 1/2252 73/863.03 |
| 6,865,926 B2 | 3/2005 | O'Brien et al. | |
| 7,162,933 B2 | 1/2007 | Thompson et al. | |
| 7,484,404 B2 | 2/2009 | Thompson et al. | |
| 8,056,399 B2 | 11/2011 | Thompson et al. | |
| 9,097,695 B2 | 8/2015 | Kriel et al. | |
| 9,562,833 B2 | 2/2017 | Thompson et al. | |
| 2005/0217351 A1 * | 10/2005 | Kreck | G01N 1/16 73/64.56 |
| 2006/0201235 A1 | 9/2006 | Thompson et al. | |
| 2011/0016955 A1 | 1/2011 | Cormier et al. | |
| 2013/0263680 A1 | 10/2013 | Barere | |
| 2016/0068777 A1 * | 3/2016 | Menon | C10L 3/10 48/127.3 |
| 2018/0155649 A1 * | 6/2018 | Gerhold | C10L 3/08 |

* cited by examiner

MULTI-SOURCE, FLOW-WEIGHTED COMPOSITE SAMPLE SYSTEM

CROSS-REFERENCE TO RELATED APPLICATIONS

This application claims priority to U.S. Patent Application 62/565,865 filed on Sep. 29, 2017, the entirety of which is herein incorporated by reference.

FIELD OF INVENTION

This invention relates to a system and method for providing increased accuracy in input sample analysis from multiple discrete input sources to and/or from one or more receiving vessels, such as a stationary storage tank or a tanker ship, by accounting for flow rate differential between the respective discrete input sources.

BACKGROUND

Natural gas, like other forms of heat energy, is measure in British Thermal units, or BTU. One BTU is equivalent to the heat needed to raise the temperature of one pound of water by one-degree Fahrenheit at atmospheric pressure. Because LNG is sold in accordance with its BTU value, accurate analysis of the BTU value of any particular LNG shipment, as well as analysis of the constituent components of the LNG, as it is loaded on and off a respective tanker ship is crucial. For example, to determine an expected price for a particular shipment, when LNG is loaded onto a tanker ship at an overseas location, such as Trinidad and Tobago, the supplier calculates the BTU value of the LNG as it is loaded into the hull of the ship. Thus, the operator of the tanker ship carrying the LNG shipment is keenly interested in accurate BTU measurement of both the loaded LNG as well as the off-loaded LNG as the shipper typically burns the LNG vaporized in transit to run the ship and, thus, is responsible for cost of the LNG vaporized in transit.

Presently, if a LNG tanker is being loaded from multiple storage tanks or a series of railroad tanker cars, using, for example, two to four different pipelines, there is no device or method to generate accurate composite data from the combined inputs and account for variations in flow rates of each of the discrete inputs during the transfer/loading process. This problem applies similarly in the context of one or more tankers and/or railroad tanker cars using multiple pipelines to load one or more tanks and/or one or more railroad tanker cars.

In the context of a cryogenic LNG, for example, cargo loads are often composed of simultaneously transferred inputs from different storage vessels containing different compositions or other physical properties. The flow rates may vary between the input from respective sources, which leaves the operator to essentially guess or guesstimate the contributions from each source and apply that obtained estimated number to the determined energy content/composition analysis of the resulting transferred mixture.

When time-elapse composite sampling of a multi-input mixture is processed through a composite system as along the lines of that described in U.S. Pat. No. 9,562,833, the use of relative flow rate guesstimates for analytical purposes becomes unreliable, imprecise and untenable.

SUMMARY OF THE INVENTION

The present invention envisions a solution providing a single analytical system capable of providing an accurate composite sample obtained from multiple input sources for energy content/composition analysis which reflects the variations in the input flow rates from the respective sources. The present invention can be utilized as a stand-alone unit or as an adjunct to an existing system, such as for example, the Mustang® Composite Sampling System (MCSS™), an intermittent, waterless sampling system for liquefied natural gas which is compliant with the requirements of ISO 8943 and which is capable of accumulating a representative sample by capturing small samples at regular intervals, either fixed or proportional to flow rate. Such a system is available from Mustang Sampling, LLC of Ravenswood, W. Va. and is an embodiment of a Composite Sampling System described in U.S. Pat. No. 9,562,833, the entirety of which is herein incorporated by reference.

The system and method of the present invention consolidates the equipment requirements that would otherwise be required for each discrete sample take off source.

The invention described herein contemplates combinational sampling by a system with the capability of providing composite samples from multiple discrete input sources and accounts for the flow rate of each of the admixed inputs for energy content/compositional analysis of natural gas.

In the context of an LNG system, the multi-source sampling system provides an accurate sample for analysis from a plurality of sources, e.g. two or more, which are later combined. Thus, the BTU value of LNG loaded on to a tanker from various input sources or off-loaded to a tank or railroad tanker car from various input sources can be accurately determined as well as the constituent components of the LNG.

The system relies on an input from each discrete source being monitored and controlled by a mass flow meter that is set to correspond to the established rate of flow for that particular source (e.g. pipeline). By way of example, if a first tanker car takeoff pipeline has a 60% flow rate and a second tanker car takeoff pipeline has a 40% flow rate with respect to the total flow rate of sample to enter a tanker, the respective total volumetric flow rates through respective mass flow controllers are adjusted to each provide a throughput to a common vapor sample accumulator that corresponds to the proportional, native flow rates of the respective sources. The system also permits samples to be extracted and analyzed from at least one active source even when one or more of the discrete sources is shut down with no flow.

In short, the invention contemplates that prior to analysis, vaporized gas samples from discrete sources which can be from a sample probe or a sample conditioning system are combined into an accumulator chamber in a calculated ratio. This ratio reflects the respective flow ratios between the discrete sources. For the purpose of discussion, although the following description contemplates a two-source stream embodiment, the inventive concept is not so limited and could include any number of sources. In the case of a two-source input, the flow of vaporized gas into the accumulator is controlled by means of two mass flow controllers, one for each source, to generate a composition sample proportional to the input flows. Each vaporized gas stream exiting the mass flow controller is introduced into the mixing accumulator through an accumulator impingement tube/mixing wand projecting into the interior of the accumulator. As a result, an output from the accumulator is a mixture of the input gases and will be identical to the final mixture involved in the transfer loading, and, therefore, appropriate for analysis as the final combined cargo load. If a system includes additional input sources, e.g. five or six, each additional input is associated with one or more mass flow controllers.

The system includes a device capable of measuring proportional flow rate and capable of determining an effective (flow weighted) composition or energy value for multiple streams, regardless of different flow ratios, without the addition of a dedicated sampling point and its associated equipment. This provides for the ability to blend LNG while avoiding the issue of dew point dropout.

It is an object of the present invention to overcome the aforementioned problems associated with conventional structures of the prior art such as with compositional analysis of LNG flow from multiple input and/or output flow paths.

It is therefore an object of the present invention to provide a system, device and method for conveniently and more accurately measuring the composition of product from multiple sources being onloaded to or offloaded from a vessel such as a tank, tanker, barge, truck, or railroad tanker car.

It is a further object of the present invention to provide for enhanced proportional compositional analysis with respect to multiple input and/or output flow paths of product such that the percentage composition based on flow rate can be determined for each path.

Still yet another object of the present invention is to provide for more accurate calculation of compositional and/or BTU values for both onloaded and offloaded LNG thereby allowing for enhanced sales transactions of LNG.

Objects of the invention are satisfied by a system for capturing a composite gas sample from multiple input sources during transfer processing, comprising: at least a first and a second feedstock input lines; a sample takeoff assembly associated with each input line for extracting samples from said feedstock input lines; a sampling device having a mass flow controller associated with each sample takeoff assembly, each mass flow controller having a sample output and being configured to receive a signal representative of the flow rate from each of said first and second feedstock input lines, where each mass flow controller adjusts the flow rate of its respective sample from its respective sample output in response to receiving representative signals; at least a first and second sample output line respectively connected with the sample output of each mass flow controller, each sample output line being connected to an input of a sample accumulator for introduction to the sample accumulator of samples from the output of the mass flow controllers.

Further objects of the invention are met by a sampling device, comprising: at least two inputs each configured to receive samples from a corresponding feedstock input line; a sample accumulator; a mass flow controller associated with each feedstock input line, each mass flow controller having a sample output and being configured to receive a signal representative of the flow rate at each input, where each mass flow controller adjusts the flow rate of its respective sample from its respective sample output in response to receiving representative signals; and at least a first and second sample output line respectively connected with a sample output of each mass flow controller, each sample output line being connected to an input of the sample accumulator for introduction to the sample accumulator of samples from the output of the mass flow controllers.

Further objects of the invention are met by a method for accounting for the flow rate from a plurality of sample fluid sources to a combined input for increased measurement accuracy in energy content/composition analysis, the method comprising: determining the flow rate of a sample fluid in each of the plurality of sample fluid sources; extracting a sample from each of the plurality of sample fluid sources; passing each such extracted sample to and inputting such sample into a common sample accumulator at an adjusted flow rate corresponding to the determined flow rate of its sample fluid source; accumulating a plurality of fluid samples in the accumulator to create a composite sample; and outputting a select amount of said composite sample from the accumulator for energy content/compositional analysis of the composite sample.

DESCRIPTION OF THE ILLUSTRATIONS

As used herein "substantially", "relatively", "generally", "about", and "approximately" are relative modifiers intended to indicate permissible variation from the characteristic so modified. They are not intended to be limited to the absolute value or characteristic which it modifies but rather approaching or approximating such a physical or functional characteristic.

In the detailed description, references to "one embodiment", "an embodiment", or "in embodiments" mean that the feature being referred to is included in at least one embodiment of the invention. Moreover, separate references to "one embodiment", "an embodiment", or "in embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

It will be appreciated that as used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

It will also be appreciated that as used herein, any reference to a range of values is intended to encompass every value within that range, including the endpoints of said ranges, unless expressly stated to the contrary.

Figure 1:
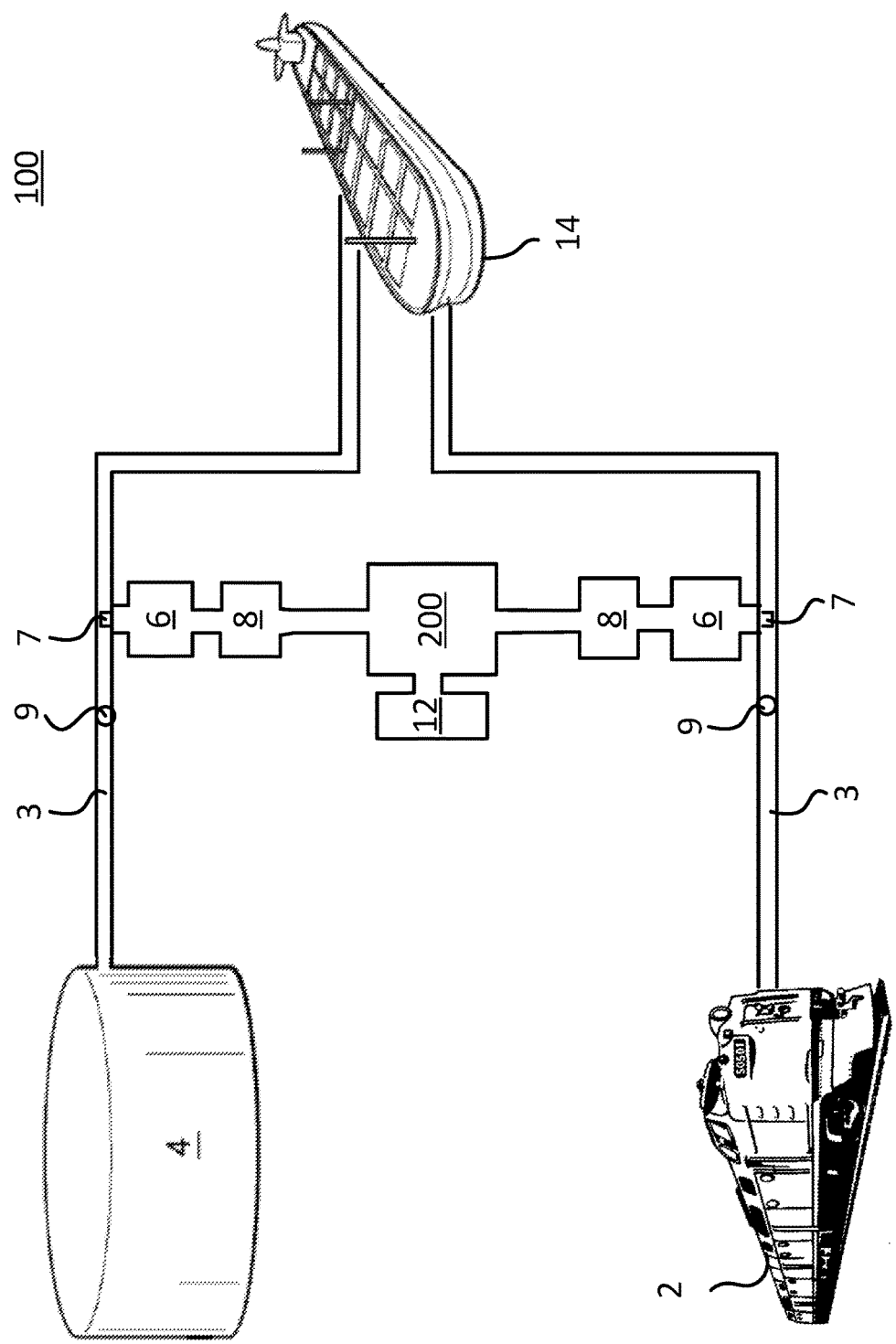
FIG. 1 is a block diagram illustrating a system in accordance with the present invention.

FIG. 1 is a block diagram illustrating a system 100 for transferring gas, such as LNG, from a tank 4 and railroad tanker car 2 to a tanker 14. However, the description herein is not limited to such an example and LNG could be transferred between various sources such as from two tanks into a third tank. Initially, the LNG from both the tank 4 and railroad tanker car 2 are transferred towards tanker 14 on respective gas streams/lines 3. As the LNG travels towards tanker 14 on respective lines/streams 3, the flow rate of LNG in each respective stream/line 3 is measured and recorded by sensors 9 and samples of the LNG are extracted via corresponding take-off probes 7, preferably conforming to requirements of ASME B31.3-214, such as a Certiprobe® available from Mustang Sampling, LLC of Ravenswood, W. Va. In one example, each sensor 9 can be incorporated with a respective take-off probe 7 such that the flow rate is measured at the point at which LNG is extracted from the input streams/lines 3. The LNG extracted from each take-off probe 7 may then be passed to a vaporizer 6 of, for example, of the type described in U.S. Pat. No. 8,056,399. The vaporized, extracted LNG sample is then conditioned and regulated to prevent hydrocarbon liquid condensation from Joule-Thomson cooling, etc. by a single or redundant multipath sample conditioning system 8. An exemplary system for obtaining extracted conditioned samples consistent with these objectives and capable for use with the invention herein, is a Mustang Intelligent Vaporizer Sampling System available from Mustang Sampling, LLC of Ravenswood W. Va. and/or a system of the type illustrated and described in U.S. Pat. No. 9,057,668, the entirety of which is herein incorporated by reference. Once the LNG sample from the sources, e.g. tank 4 and railroad tanker car 2, has been converted to vapor by the vaporizers 6 and passed through the downstream sample conditioners 8, the conditioned sample streams are introduced into, accumulated, and homogenized by multi-source, flow-weighted sample system 200. Although not illustrated, in one example, the system 100 may include only one vaporizer 6 and sample conditioning system 8 which receive input from each stream/line 3 to process all streams/lines 3 of the system 100 at which point the sample streams can be output from the sample conditioning system 8 to the system 200.

Figure 2:
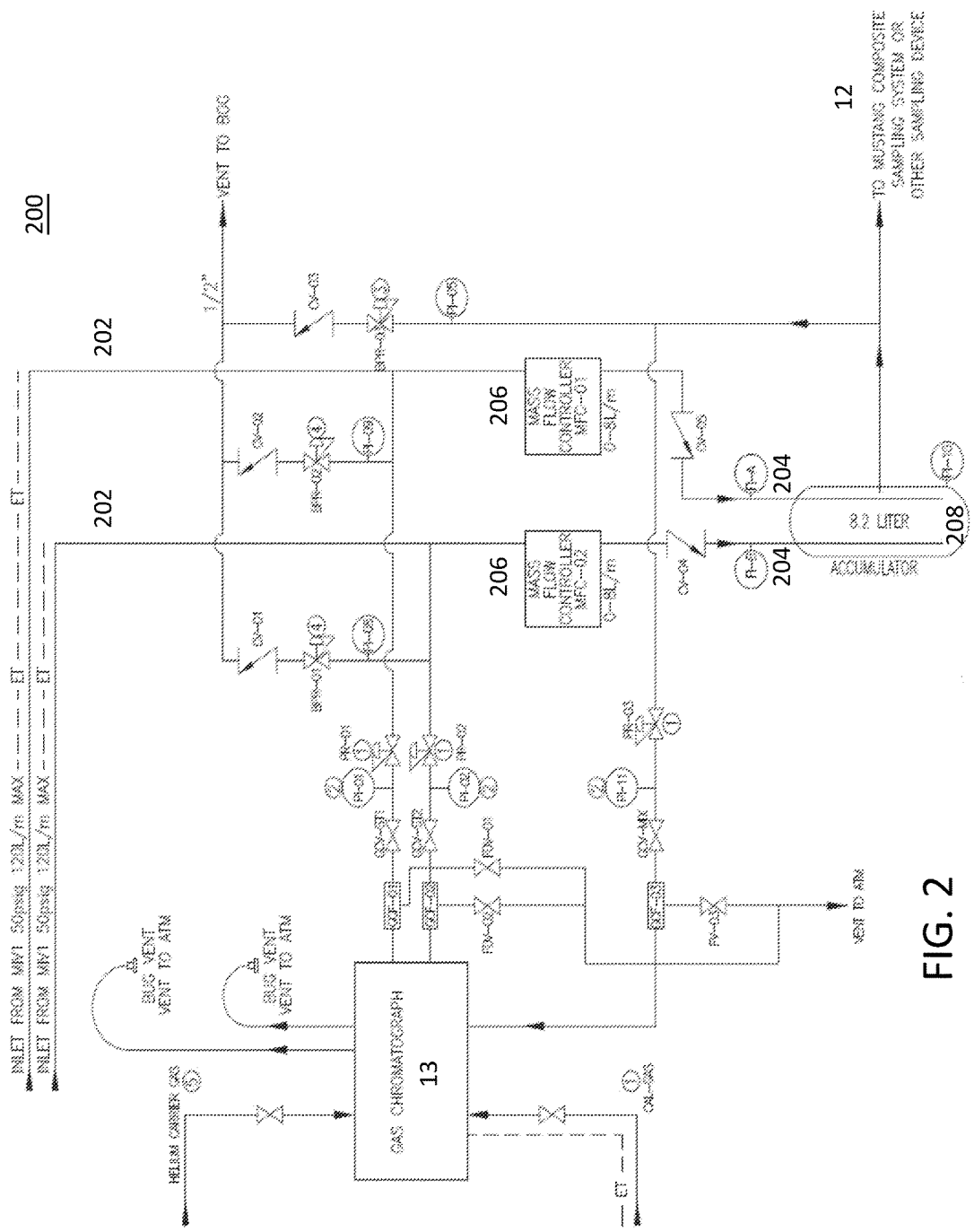
FIG. 2 is a schematic representation of an embodiment of the multi-source, flow-weighted composited sample system in the context of a binary (two input) system.

FIG. 2 schematically represents an example of the sample system 200 according to a binary embodiment of the invention. The illustrated sample system 200 adapted for use in the case of two parallel input sources (e.g., from a group consisting of one or more tanker trucks, railcars and storage tanks) contemplates a number of inlet lines 202 corresponding to the number of input streams/lines 3. Therefore, each input inlet line 202 corresponds to a respective output of a sample conditioner 8. Accordingly, as illustrated, the flow of each sample inlet 202 is controlled by a corresponding MFC 206. The MFCs 206 can be separated or as part of an overall MFC unit having multiple inputs, multiple MFCs 206 and multiple respective outputs. In the case of the illustrated binary system, the two MFCs 206 have circuitry that is in electronic signal communication with an Allen Bradley 850 series Programmable Logic Controller (PLC) or equivalent digital controller. In the illustrated example, the MFCs 206 are in the form of conventional mass flow controllers. As used herein, MFC is intended to include any conventional flow control means whether volumetric, ratio, differential, turbine, rotor, ultrasonic and/or Coriolis.

The PLC, itself, is in remote signal communication with and may be controlled by a Distributed Control System (DCS) or an adequate equivalent communications control system. The DCS monitors the flow rates of each respective transfer stream/line 3 by processing appropriate flow sensor 9 readings and transmits by way of a conventional communication protocol, such as a MODBUS Remote Terminal Unit (RTU), a percentage (%) flow setting for the respective MFC 206 to the PLC. This represents the percentage (%) flow of each respective transfer line 3 measured by the sensors 9 which contributes to the combined sample where the total for the combined percentages totals 100%. The PLC then transmits one or more signals to each MFC 206 identifying the percentage (%) flow for each respective transfer line based on the data received from the DCS. Each MFC 206 receives the one or more signals and adjusts a flow rate of a respective line 3 accordingly such that the vapor output of each MFC 206 from each line 3 corresponds to the detected flow rate of the corresponding line 3. In one example, each MFC 206 can control the flow rate of its respective line 3 by use of a solenoid valve.

The output from each of the respective MFCs 206 is then communicated via a respective output line 204 to a mixing accumulator 208 with impingement tubes/wand that can be of a type described and disclosed in U.S. Pat. No. 8,056,399. This admixed sample represents the combination of the inputs received from the two transfer sources (i.e. tank 4 and railroad tanker car 2) to the receiving vessel which may be a ship (i.e. tanker 14) or large static storage facility. The admixed sample output from the mixing accumulator 208 can be directed to a selected destination such as an analyzer/gas chromatograph 13 for energy content/compositional analysis such as the gas chromatograph described in U.S. Pat. No. 8,056,399 or to the Mustang® composite sampling system or grab cylinder array 12 such as that described previously herein and in the above-referenced U.S. Pat. No. 9,562,833.

As illustrated in FIG. 2, the sample system 200 further includes inputs to the gas chromatograph 13 for receiving the input vapor samples from each input inlet line 202 for directly sampling the sample vapors for energy content/composition prior to input of the vaporized samples into the respective MFCs 206. This allows the sample system 200 to generate composition data prior to flow rate control by the MFCs 206 thereby allowing the sample system 200 to generate test data for testing and calibration of the sample system 200. Further, each input line from the inlet input to the gas chromatograph 13 can include one or more check valves controlled by the PLC to shunt one line should it be desired to analyze the streams individually.

Figure 3:
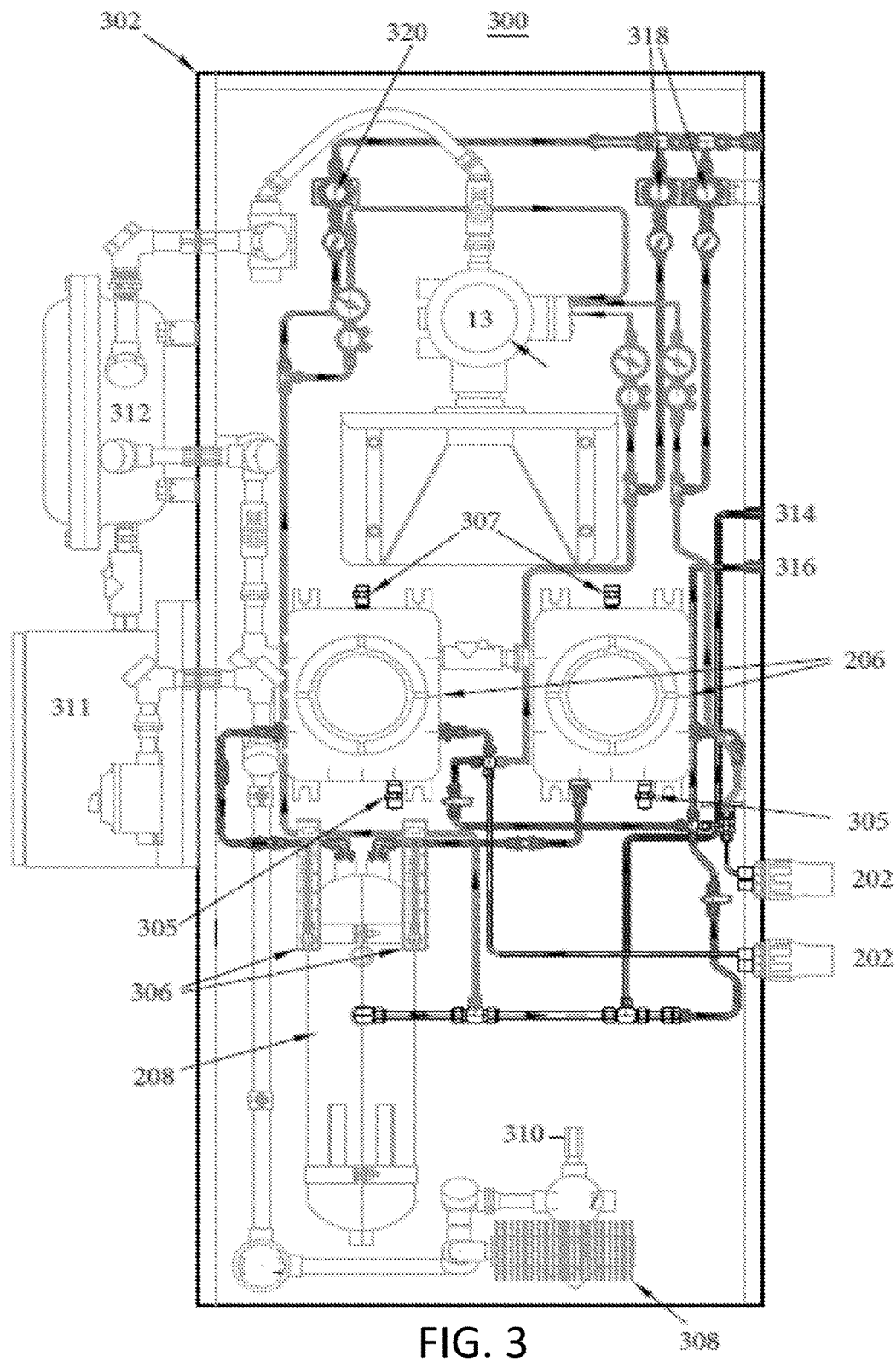
FIG. 3 is a schematic representation of an equipment cabinet according to an embodiment of the invention.

FIG. 3 is a schematic representation of an equipment cabinet 300 for housing the sample system 200 according to an embodiment of the invention. As FIG. 3 illustrates an enclosure of the sample system 200 illustrated in FIG. 2, like designations are repeated. The equipment cabinet 300 includes a housing 302 having configured therein two MFCs 206, the mixing accumulator 208, flow meters 306 corresponding to the output of each MFC 206, the gas chromatograph 13, drains 305 to remove moisture or excess liquid, breathers 307 for equalizing the enclosure to prevent explosions, a heater 308 to maintain temperature regulation of the composite sample and a thermostat 310 operating in conjunction with the heater 308. Although FIG. 3 depicts only two mass flow controllers 206, it is understood that the description herein is not limited to this depiction and that the equipment cabinet 300 could house additional MFCs 206 for processing additional input lines or that one MFC with multiple inputs and outputs could be used to control flow rates of multiple lines. The admixed sample output from the mixing accumulator 208 can be output to a Mustang® composite sampling system via a first output 314 and/or to a grab cylinder array via a second output 316.

FIG. 3 also illustrates a first enclosure 311 for housing input power to the sample system 200 and a second enclosure 312 for housing the PLC and DCS processing circuitry. Alternatively, the DCS could be remotely located and in direct or wireless communication with the PLC. The first enclosure 311 can provide a visual indicator for field verification of the actual flow meter percentage flow rate. In addition to, or alternatively, the actual flow meter percentage flow rate information can be transmitted via the PLC to the DCS for remote notification and verification. The equipment cabinet 300 further includes a plurality of pressure regulators 318 and 320. The pressure regulators 318 maintain the appropriate pressure internally for the incoming input vapor samples received on the input inlet lines 202. In other words, the pressure regulators 318 ensure the appropriate pressure on individual lines based on the percentage flow setting of each MFC 206. The pressure regulator 320 may be a forward or back pressure regulator so long as it maintains the appropriate pressure for the admixed sample output from the mixing accumulator 208.

FIG. 3 illustrates one example of a housing for the sample system 200. However, the invention is not limited to such a composition and additional embodiments are contemplated. It is therefore understood that the invention is not limited to the specific embodiment disclosed herein, and that many modifications and other embodiments of the invention are intended to be included within the scope of the invention. Moreover, although specific terms are employed herein, they are used only in generic and descriptive sense, and not for the purposes of limiting the description of the invention.

Further, although an illustrated binary embodiment of the invention has been described in the forgoing specification, it is understood by those skilled in the art that many modifications and embodiments of the invention will come to mind to which the invention pertains, having benefit of the teaching presented in the foregoing description and associated drawing. For example, a system with four, five, six or more inputs, each being subject to proportional weighting, would fall within the scope of the invention. Also, while primarily disclosed in the context of LNG, a cryogenic, the invention is applicable to analysis of combined non-cryogenic fluids. It is therefore understood that the invention is not limited to the specific embodiment disclosed herein, and that many modifications and other embodiments of the invention are intended to be included within the scope of the invention. Moreover, although specific terms are employed herein, they are used only in generic and descriptive sense, and not for the purposes of limiting the description of the invention.

We claim:

1. A system for capturing a composite sample from multiple input sources during transfer processing, comprising:
   at least a first and a second feedstock input line;
   at least a first and a second flow rate sensor attached to the first and second feedstock input lines respectively;
   a sample takeoff assembly associated with each feedstock input line for extracting samples from said feedstock input lines;
   a sampling device having a mass flow controller associated with each sample takeoff assembly, each mass flow controller having a sample output and being configured to receive a signal representative of the flow rate in each of said first and second feedstock input lines, from said first and second flow rate sensors, where each mass flow controller adjusts the flow rate of its respective sample output in response to receiving said representative signals;
   at least a first and second sample output line respectively connected with the sample output of each mass flow controller, each sample output line being connected to an input of a sample accumulator for introduction to the sample accumulator of samples from the output of the mass flow controllers.

2. The system of claim 1 where the sample takeoff assembly includes a feedstock sample output for direct sampling of an extracted sample for analysis of at least one of energy content or composition prior to input to the sample accumulator.

3. The system of claim 1 further including a sample vaporizer and a sample conditioner associated with each of the at least respective first and second input lines.

4. The system of claim 3 where each sample vaporizer receives and vaporizes samples received from an output of a respective sample takeoff assembly.

5. The system of claim 4 where each sample conditioner receives and conditions vaporized samples received from an output of a respective vaporizer.

6. The system of claim 5 where the sampling device receives as respective samples the conditioned samples from each sample conditioner.

7. The system of claim 1 where an output of the sample accumulator is connected to a composite sampling system.

8. The system of claim 1 where an output of the sample accumulator is connected to an analyzer for analysis of at least one of energy content or composition of the accumulated sample.

9. A sampling device, comprising:
   at least two inputs each configured to receive samples from a corresponding feedstock input line;
   a sample accumulator;
   a mass flow controller associated with each feedstock input line, each mass flow controller having a sample output and being configured to receive a signal representative of the flow rate at each input, from a flow rate sensor on each feedstock input line, where each mass flow controller adjusts the flow rate of its respective sample from its respective sample output in response to receiving said representative signals; and
   at least a first and second sample output line respectively connected with a sample output of each mass flow controller, each sample output line being connected to an input of the sample accumulator for introduction to the sample accumulator of samples from the output of the mass flow controllers.

10. The sampling device of claim 9 where the sampling device includes an analyzing device connected to each input for direct sampling of received samples for analysis of at least one of energy content or composition prior to input to respective mass flow controllers.

11. The sampling device of claim 9 where the sampling device receives samples processed by a sample vaporizer and a sample conditioner associated with each of the at least respective first and second input lines.

12. The sampling device of claim 9 where an output of the sample accumulator is connected to a composite gas sampling system.

13. The sampling device of claim 9 where an output of the sample accumulator is connected to an analyzer for analysis of at least one of energy content or composition of the accumulated sample.

14. A method for accounting for the flow rate from a plurality of sample fluid sources to a combined input for increased measurement accuracy in analysis of at least one of energy content or composition, the method comprising:

determining the flow rate of a sample fluid in each of the plurality of sample fluid sources;

extracting a sample from each of the plurality of sample fluid sources;

passing each such extracted sample to and inputting such sample into a sample accumulator at an adjusted flow rate that is proportional to the determined flow rate of its sample fluid source;

accumulating a plurality of fluid samples in the accumulator to create a composite sample; and outputting a select amount of said composite sample from the accumulator for analysis of at least one of energy content or composition of the composite sample.

15. The method of claim 14 where the analysis of at least one of energy content or composition is performed by a gas chromatograph.

16. The method of claim 14 where each extracted sample is processed by a respective vaporizer to vaporize the sample prior to being passed into the sample accumulator.

17. The method of claim 16 where each vaporized sample is processed by a sample conditioner to condition the samples prior to being passed into the sample accumulator.

18. The method of claim 14 further comprising outputting a select amount of said composite sample to a composite sampling system.

\* \* \* \* \*